United States Patent
Tanabe (10) Patent No.: US 11,073,576 B2
(45) Date of Patent: Jul. 27, 2021

(54) MAGNETIC FIELD DETECTION DEVICE AND MAGNETIC FIELD DETECTION METHOD

(71) Applicant: TDK CORPORATION, Tokyo (JP)

(72) Inventor: Kei Tanabe, Tokyo (JP)

(73) Assignee: TDK CORPORATION, Tokyo (JP)

( * ) Notice: Subject to any disclaimer, the term of this patent is extended or adjusted under 35 U.S.C. 154(b) by 460 days.

(21) Appl. No.: 15/770,195

(22) PCT Filed: Oct. 20, 2016

(86) PCT No.: PCT/JP2016/081102
§ 371 (c)(1),
(2) Date: Apr. 21, 2018

(87) PCT Pub. No.: WO2017/077870
PCT Pub. Date: May 11, 2017

(65) Prior Publication Data
US 2018/0321332 A1   Nov. 8, 2018

(30) Foreign Application Priority Data

Nov. 4, 2015 (JP) .............................. JP2015-216285

(51) Int. Cl.
*G01R 33/09* (2006.01)
*G01R 33/025* (2006.01)
(Continued)

(52) U.S. Cl.
CPC ....... *G01R 33/091* (2013.01); *G01R 33/0023* (2013.01); *G01R 33/025* (2013.01);
(Continued)

(58) Field of Classification Search
CPC .. G01R 33/0041; G01R 33/09; G01R 33/093; G01R 33/025; G01R 33/07;
(Continued)

(56) References Cited

U.S. PATENT DOCUMENTS

2011/0133733 A1*  6/2011  Nagasaki ............. G01R 33/063
                                                        324/252
2015/0115938 A1*  4/2015  Kasajima ........... G01R 33/0041
                                                        324/207.18

FOREIGN PATENT DOCUMENTS

| CN | 102353911 A | 2/2012 |
| JP | 2009297224 A | 12/2009 |
| JP | 2012152515 A | 8/2012 |

\* cited by examiner

*Primary Examiner* — Amy He
(74) *Attorney, Agent, or Firm* — Young Law Firm, P.C.

(57) ABSTRACT

An object of the present invention is to selectively detect a detection magnetic field without separately providing a sensor for detecting an environmental magnetic field. A magnetic field detection device includes a magnetic field detection unit 10 that generates an output signal S1 according to a magnetic field, a first signal generation unit 20 that extracts a predetermined frequency component from the output signal S1 and generates a cancel signal S2 based on the predetermined frequency component, a first magnetic field generation unit 40 that applies a first cancel magnetic field to the magnetic field detection unit 10 based on the cancel signal S2, and a second signal generation unit 30 that generates a detection signal S3 based on the output signal S1 of the magnetic field detection unit 10 to which the first cancel magnetic field is applied. According to the present invention, a cancel signal is generated based on a frequency component of an output signal, and a first cancel magnetic field is applied to a magnetic field detection unit using the cancel signal. Therefore, it is not necessary to separately provide a sensor for detecting an environmental magnetic field. Because this configuration reduces the number of parts, downsizing and cost reduction can be realized.

12 Claims, 12 Drawing Sheets

(51) Int. Cl.
  *G01R 33/00*  (2006.01)
  *A61B 5/05*  (2021.01)

(52) U.S. Cl.
  CPC ........... *G01R 33/09* (2013.01); *G01R 33/093* (2013.01); *G01R 33/095* (2013.01); *A61B 5/05* (2013.01)

(58) Field of Classification Search
  CPC .. G01R 33/0029; G01R 33/007; G01R 33/02; G01R 33/035; G01R 33/091; G01R 33/0023; G01R 33/095; B82Y 25/00; A61B 5/05
  See application file for complete search history.

MAGNETIC FIELD DETECTION DEVICE AND MAGNETIC FIELD DETECTION METHOD

TECHNICAL FIELD

The present invention relates to a magnetic field detection device and a magnetic field detection method, and more particularly relates to a magnetic field detection device and a magnetic field detection method that selectively detect a detection magnetic field by canceling an environmental magnetic field superimposed on the detection magnetic field.

BACKGROUND ART

A magnetic field detection device that detects a weak magnetic field emitted from a human body or the like is strongly influenced by an environmental magnetic field such as terrestrial magnetism. Therefore, it is essential in this type of device to cancel the influences of the environmental magnetic field.

A magnetic field detection device described in Patent Document 1 has a sensor that detects an environmental magnetic field separately from a sensor that detects a magnetic field to be measured, and drives a cancel coil based on an output signal of the separately-provided sensor to cancel the environmental magnetic field. A magnetic field detection device described in Patent Document 2 also has a sensor that detects an environmental magnetic field separately from a sensor that detects a magnetic field to be measured, and calculates a difference between output signals of these sensors to extract a component of the magnetic field to be detected.

CITATION LIST

Patent Document

Patent Document 1: Japanese Patent Application Laid-open No. 2009-297224
Patent Document 2: Japanese Patent Application Laid-open No. 2012-152515

SUMMARY OF INVENTION

Technical Problem to be Solved by Invention

However, because both magnetic field detection devices described in Patent Documents 1 and 2 separately require a sensor that detects an environmental magnetic field, these magnetic-field detection devices have a problem that the number of parts is increased and cost reduction is difficult to realize.

It is therefore an object of the present invention to provide a magnetic field detection device and a magnetic field detection method that can selectively detect a detection magnetic field without separately providing a sensor for detecting an environmental magnetic field.

Means for Solving Problem

A magnetic field detection device according to the present invention comprises a magnetic field detection unit that generates an output signal according to a magnetic field, a first signal generation unit that extracts a predetermined frequency component from the output signal and generates a cancel signal based on the predetermined frequency component, a first magnetic field generation unit that applies a first cancel magnetic field to the magnetic field detection unit based on the cancel signal, and a second signal generation unit that generates a detection signal based on the output signal of the magnetic field detection unit to which the first cancel magnetic field is applied.

According to the present invention, a cancel signal is generated based on a frequency component of an output signal, and a first cancel magnetic field is applied to a magnetic field detection unit using the cancel signal. Therefore, it is not necessary to separately provide a sensor for detecting an environmental magnetic field. Because this configuration reduces the number of parts, downsizing and cost reduction can be realized.

In the present invention, it is preferable that the predetermined frequency component includes a DC component. Accordingly, a detection magnetic field can be measured in a state where terrestrial magnetism has been canceled.

In the present invention, the first signal generation unit can include a low-pass filter, a band elimination filter, a high-pass filter, or a band-pass filter, or can include an A/D converter that converts the output signal into a digital signal, and a digital filter that processes the digital signal.

In the present invention, it is preferable that the first magnetic field generation unit includes a first coil and that the magnetic field detection unit is placed in an inner diameter portion of the first coil. This enables an environmental magnetic field to be canceled more accurately.

It is preferable that the magnetic field detection device according to the present invention further includes a second magnetic field generation unit that applies a second cancel magnetic field to the magnetic field detection unit based on the output signal of the magnetic field detection unit to which the first cancel magnetic field is applied. Accordingly, more accurate detection of a magnetic field can be performed by so-called closed loop control.

It is preferable that the magnetic field detection unit includes a magnetic field detection element that converts the magnetic field into a potential difference, and a first amplification circuit that amplifies the potential difference to generate the output signal. In this case, the magnetic field detection element and the second magnetic field generation unit can be integrated on a same sensor chip, or the first magnetic field generation unit can be integrated further on the sensor chip.

In the present invention, it is preferable that the magnetic field detection unit further includes a second amplification circuit that is provided separately from the first amplification circuit and that amplifies the potential difference to generate the detection signal. Accordingly, the load of each of the amplification circuits is reduced and circuit constants thereof can be set independently from each other.

A magnetic field detection method according to the present invention comprises detecting a synthetic magnetic field having an environmental magnetic field superimposed on a detection magnetic field to generate an output signal, extracting a frequency component corresponding to the environmental magnetic field from the output signal to generate a cancel signal, and canceling the environmental magnetic field based on the cancel signal to extract a component corresponding to the detection magnetic field from the output signal.

In the present invention, because it is not necessary to separately use a sensor for detecting an environmental magnetic field, the number of parts is reduced, and downsizing and cost reduction of the magnetic field detection device can be realized.

Advantageous Effects of Invention

According to the present invention, it is possible to selectively detect a detection magnetic field without separately providing a sensor for detecting an environmental magnetic field.

MODE FOR CARRYING OUT THE INVENTION

Preferred embodiments of the present invention will now be explained in detail with reference to the drawings.

Figure 1:
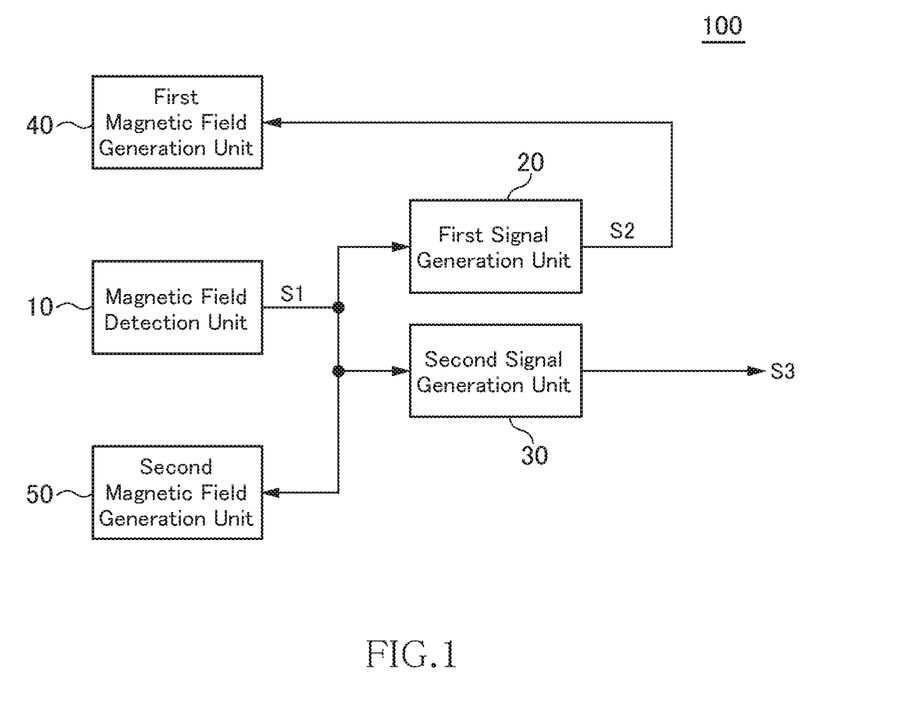
FIG. 1 is a block diagram illustrating a configuration of a magnetic field detection device 100 according to a first embodiment of the present invention.
Figure 2:
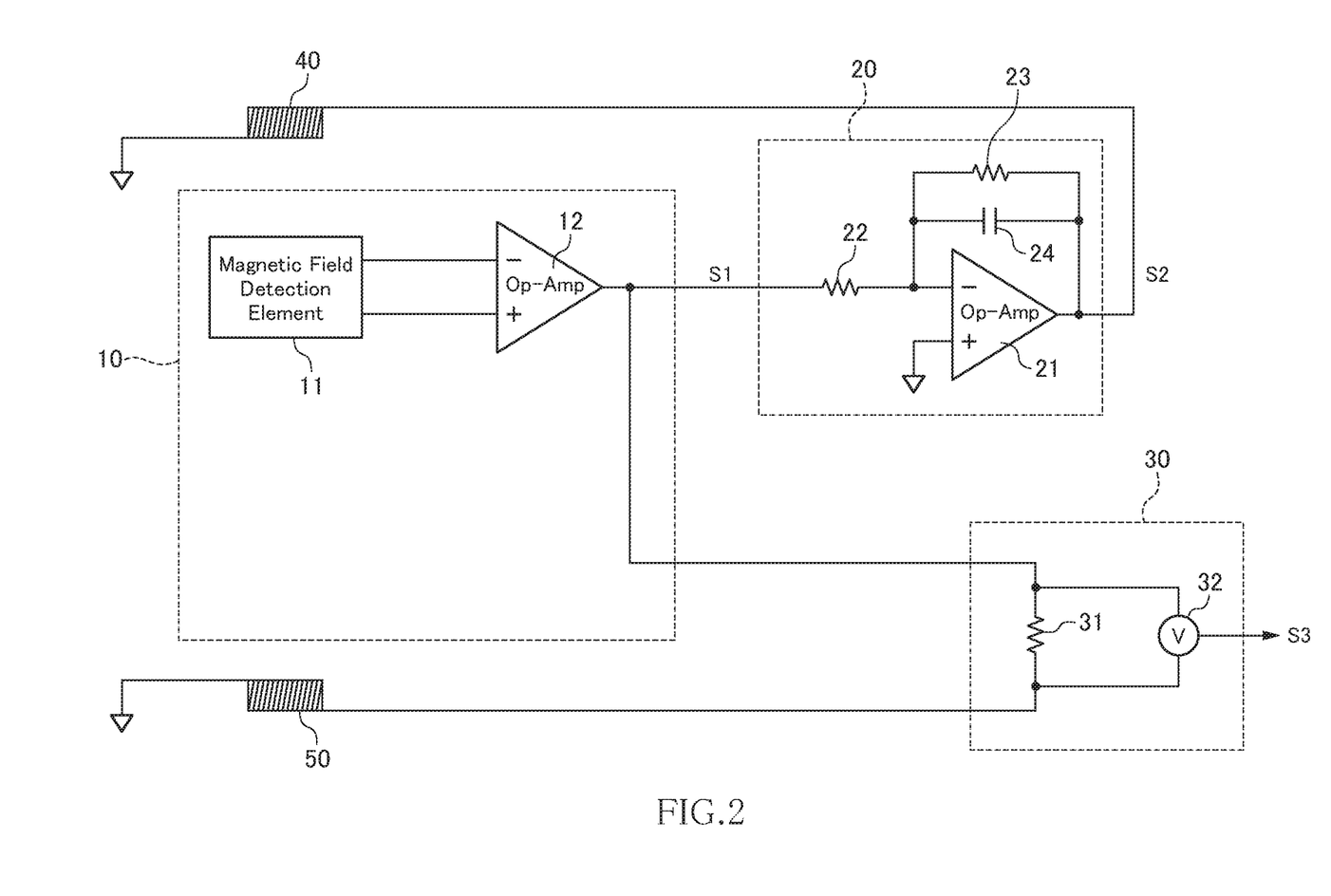
FIG. 2 is a circuit diagram illustrating an example of a specific configuration of the magnetic field detection device 100.

FIG. 1 is a block diagram illustrating a configuration of a magnetic field detection device 100 according to the first embodiment of the present invention. FIG. 2 is a circuit diagram illustrating an example of a specific configuration of the magnetic field detection device 100.

As illustrated in FIGS. 1 and 2, the magnetic field detection device 100 according to the present embodiment includes a magnetic field detection unit 10 that generates an output signal S1, a first signal generation unit 20 and a second signal generation unit 30 that receive the output signal S1, and a first magnetic field generation unit 40 and a second magnetic field generation unit 50 that apply a magnetic field to the magnetic field detection unit 10.

The magnetic field detection unit 10 is a circuit that changes the level of the output signal S1 according to a magnetic field and is placed near a detection target object to perform detection of a magnetic field (a detection magnetic field) to be detected. However, because an environmental magnetic field is superimposed on the detection magnetic field, the magnetic field detection unit 10 detects a synthetic magnetic field including the environmental magnetic field superimposed on the detection magnetic field. Therefore, in order to extract only the component of the detection magnetic field from the synthetic magnetic field, the environmental magnetic field needs to be canceled. A typical environmental magnetic field is terrestrial magnetism. Although not particularly limited, a specific configuration of the magnetic field detection unit 10 can be constituted by a magnetic field detection element 11 that outputs a differential signal, and an operational amplifier (an amplification circuit) 12 that amplifies the differential signal output from the magnetic field detection element 11 as illustrated in FIG. 2.

Figure 3:
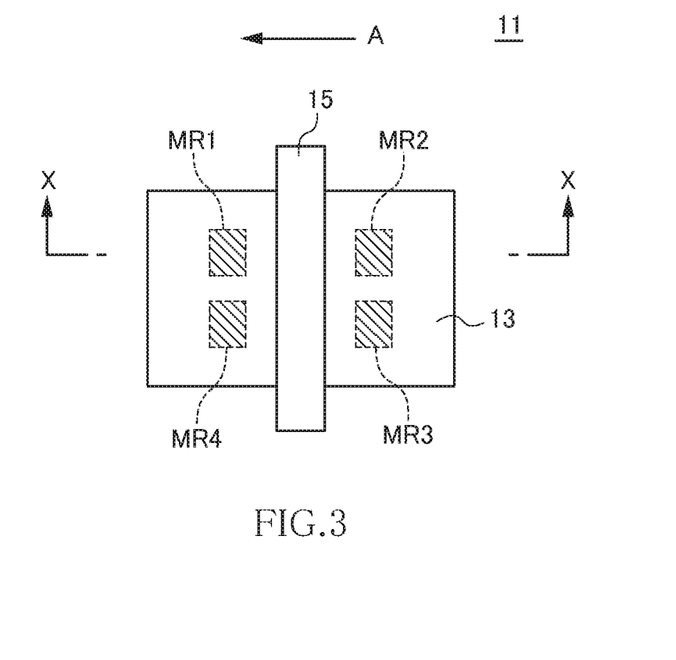
FIG. 3 is a schematic plan view illustrating an example of the magnetic field detection element 11.
Figure 4:
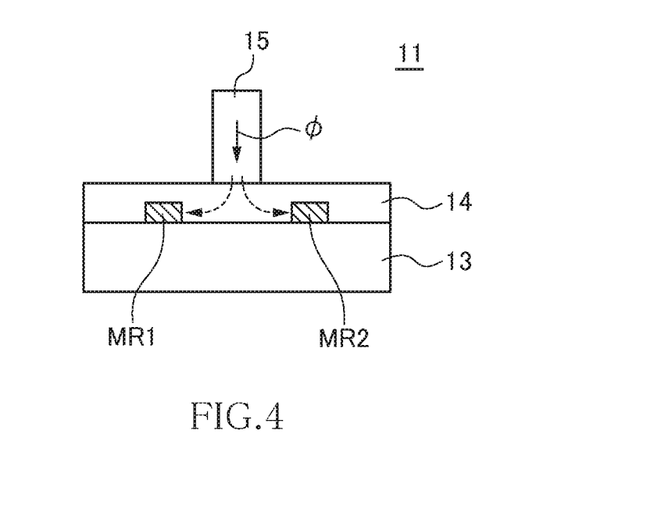
FIG. 4 is a schematic sectional view along a line X-X illustrated in FIG. 3.

FIG. 3 is a schematic plan view illustrating an example of the magnetic field detection element 11, and FIG. 4 is a schematic sectional view along a line X-X illustrated in FIG. 3.

In the examples illustrated in FIGS. 3 and 4, the magnetic field detection element 11 is a sensor chip and four magnetoresistive sensors MR1 to MR4 are provided on a substrate 13 that constitutes the sensor chip. As the magnetoresistive sensors MR1 to MR4, it is preferable to use a spin-valve-type giant magnetoresistive sensor (GMR sensor) having an electrical resistance that changes depending on the orientation of the magnetic field. Magnetization fixing directions of the magnetoresistive sensors MR1 to MR4 are all arranged to be a same direction indicated by an arrow A in FIG. 3.

A magnetic member 15 is placed on a surface of the substrate 13 with an insulating layer 14 that covers the magnetoresistive sensors MR1 to MR4 interposed therebetween. The magnetic member 15 is a block made of a highly permeable material such as ferrite and is placed between the magnetoresistive sensors MR1 and MR4 and the magnetoresistive sensors MR2 and MR3 in planar view. As illustrated in FIG. 4, the magnetic member 15 functions to collect vertical magnetic fluxes Ø, and the magnetic fluxes a collected by the magnetic member 15 are distributed to right and left substantially equally. Accordingly, the vertical magnetic fluxes Ø are provided to the magnetoresistive sensors MR1 to MR4 substantially equally.

Figure 5:
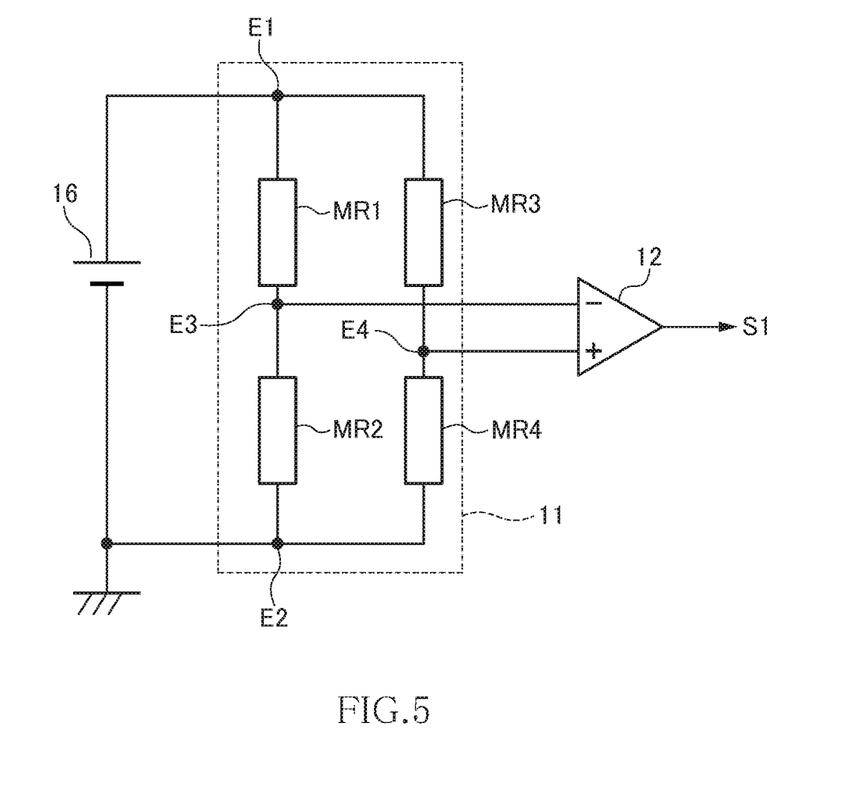
FIG. 5 is a circuit diagram for explaining a connection relation between the magnetoresistive sensors MR1 to MR4 and the operational amplifier 12.

FIG. 5 is a circuit diagram for explaining a connection relation between the magnetoresistive sensors MR1 to MR4 and the operational amplifier 12.

As illustrated in FIG. 5, the magnetoresistive sensor MR1 is connected between terminal electrodes E1 and E3, the magnetoresistive sensor MR2 is connected between terminal electrodes E2 and E3, the magnetoresistive sensor MR3 is connected between the terminal electrodes E1 and E4, and the magnetoresistive sensor MR4 is connected between the terminal electrodes E2 and E4. A predetermined voltage is applied between the terminal electrodes E1 and E2 by a constant voltage source 16. The terminal electrodes E3 and E4 are connected to input terminals of the operational amplifier 12, respectively, so that a potential difference between the terminal electrodes E3 and E4 is amplified to generate the output signal S1.

The magnetoresistive sensors MR1 and MR4 are placed on one side (on the left side in FIG. 3) of the magnetic member 15 in planar view and the magnetoresistive sensors MR2 and MR3 are placed on the other side (on the right side in FIG. 3) of the magnetic member 15 in planar view. Therefore, the magnetoresistive sensors MR1 to MR4 form a differential bridge circuit and changes in the electrical resistances of the magnetoresistive sensors MR1 to MR4 according to magnetic flux densities can be detected with high sensitivity.

That is, because all the magnetoresistive sensors MR1 to MR4 have the same magnetization fixing direction, when the magnetic fluxes from a vertical direction are bent in a horizontal direction as illustrated in FIG. 4, a difference occurs between a change amount of the resistance of the magnetoresistive sensors MR1 and MR4 located on the left side and a change amount of the resistance of the magnetoresistive sensors MR2 and MR3 located on the right side. This difference is amplified by the differential bridge circuit illustrated in FIG. 5 to be double and is amplified by the operational amplifier 12.

Referring back to FIG. 1, the output signal S1 generated by the magnetic field detection unit 10 is input to the first signal generation unit 20 and the second signal generation unit 30.

The first signal generation unit 20 is a circuit that extracts a predetermined frequency component from the output signal S1 and generates a cancel signal S2 based on the predetermined frequency component. The predetermined frequency component is a frequency component different from the frequency component of the detection magnetic field, and results from an environmental magnetic field. Because the frequency component of the detection magnetic field is known for each application, the frequency component different therefrom is a component resulting from the environmental magnetic field and is extracted by the first signal generation unit 20. As an example, when a detection magnetic field linked with heartbeat is a detection target, the frequency component of the detection magnetic field is about 100 Hz while the terrestrial magnetism being an environmental magnetic field is composed of frequency components equal to or lower than several Hz. Therefore, when a DC component included in the output signal S1 is extracted using a low-pass filter or the like, the cancel signal S2 corresponding to the terrestrial magnetism can be generated. Furthermore, in order to extract also frequency components that are emitted from a motor or the like and are higher than the detection magnetic field, a band elimination filter or the like is used to selectively eliminate frequency components near the frequency component of the detection magnetic field, so that the cancel signal S2 corresponding to the terrestrial magnetism and motor noise can be generated.

In the example illustrated in FIG. 2, the first signal generation unit 20 is a low-pass filter and includes an operational amplifier 21, resistors 22 and 23, and a capacitor 24. As illustrated in FIG. 2, the resistor 22 is connected in series to an inverting input terminal (−) of the operational amplifier 21, and the resistor 23 and the capacitor 24 are connected in parallel between an output terminal of the operational amplifier 21 and the inverting input terminal (−) A non-inverting input terminal (+) of the operational amplifier 21 is grounded. With this configuration, low-frequency components included in the output signal S1 are extracted and are output as the cancel signal S2.

The cancel signal S2 is supplied to the first magnetic field generation unit 40. The first magnetic field generation unit 40 is an element that provides a first cancel magnetic field to the magnetic field detection unit 10 based on the cancel signal S2, and a coil through which the cancel signal S2 flows can be used therefor. With this configuration, low-frequency components of the magnetic field to be applied to the magnetic field detection element 11, that is, an environmental magnetic field including terrestrial magnetism is canceled and only the detection magnetic field is applied to the magnetic field detection element 11. As a result, the output signal S1 becomes a signal substantially reflecting only the detection magnetic field.

However, because the operation to cancel an environmental magnetic field using the first magnetic field generation unit 40 is achieved by a feedback loop using the operational amplifier 21, microscopic fluctuations depending on the responsiveness of the feedback loop and the gain of the operational amplifier 21 may remain in the output signal S1. It is preferable that the frequency of such microscopic fluctuations is appropriately set to a circuit constant of the first signal generation unit 20 so as not to overlap with the frequency band of the detection magnetic field.

The output signal S1 from which influences of the environmental magnetic field have been eliminated in this way is supplied to the second signal generation unit 30. The second signal generation unit 30 includes, for example, a resistor 31 and a voltage detection circuit 32 that measures a voltage between both ends of the resistor 31, and generates a detection signal S3 corresponding to a current flowing through the resistor 31. The detection signal S3 is an output signal of the magnetic field detection device 100 according to the present embodiment and is input to another device that uses this signal.

The output signal S1 is also supplied to the second magnetic field generation unit 50, and the second magnetic field generation unit 50 provides a second cancel magnetic field to the magnetic field detection unit 10 based on the output signal S1. A coil through which the output signal S1 flows can be also used for the second magnetic field generation unit 50. Because this configuration realizes so-called closed loop control, it is possible to detect the detection magnetic field more accurately.

FIG. 6 is a diagram illustrating an operation in a case where the first signal generation unit 20 is a low-pass filter.

Figure 6A:
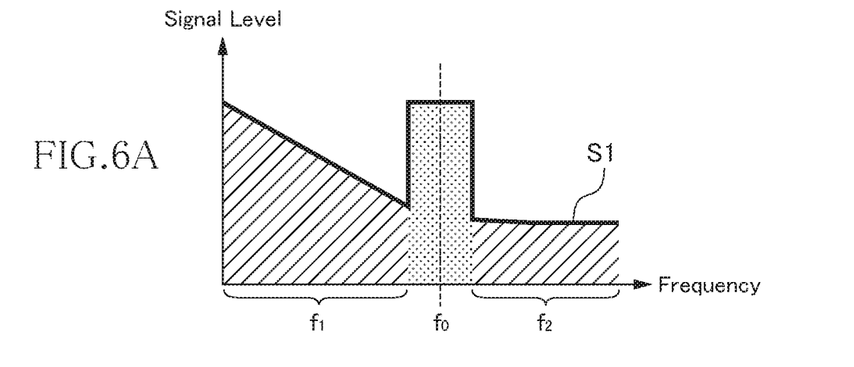
FIG. 6 is a diagram illustrating an operation in a case where the first signal generation unit 20 is a low-pass filter.
Figure 6B:
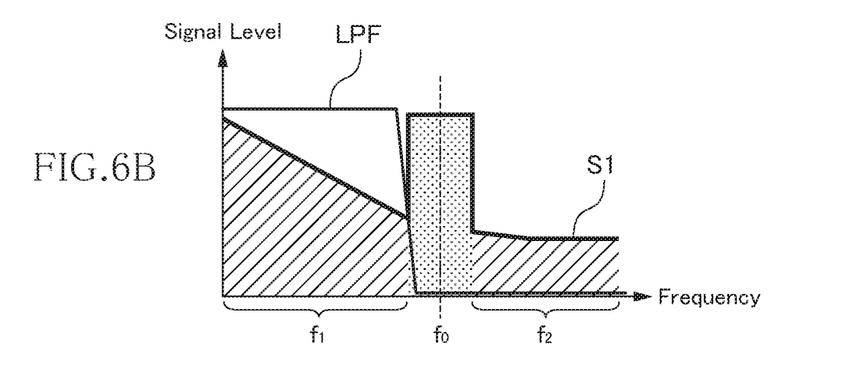
Figure 6C:
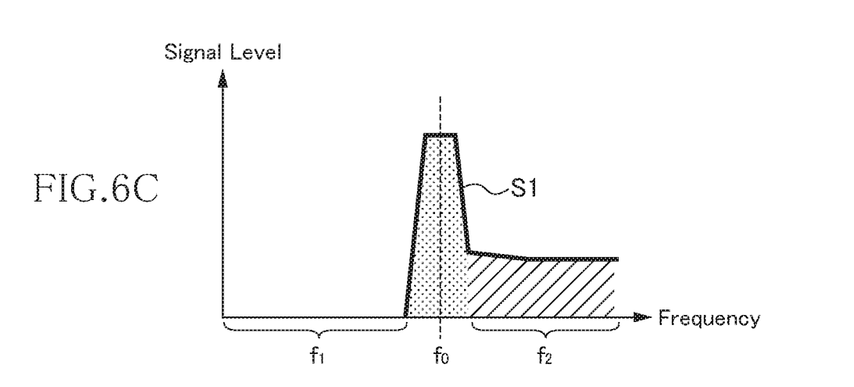

First, when the output signal S1 has frequency components illustrated in FIG. 6A and the frequency of the detection magnetic field is f0, it can be said that frequency bands f1 and f2 away from the frequency f0 of the detection magnetic field are noise components. In FIGS. 6A to 6C, the frequency bands f1 and f2 being noise are hatched and a band near the frequency f0 of the detection magnetic field is shaded.

As illustrated in FIG. 6B, the magnetic field of the frequency band f1 is canceled by the first magnetic field generation unit 40 when a low-pass filter having characteristics LPF that allow the frequency band f1 to pass is used. As a result, the frequency component f1 is eliminated from the output signal S1 as illustrated in FIG. 6C, and therefore the signal/noise (S/N) ratio becomes higher than that of the original output signal S1.

FIG. 7 is a diagram illustrating an operation in a case where the first signal generation unit 20 is a band elimination filter.

Figure 7A:
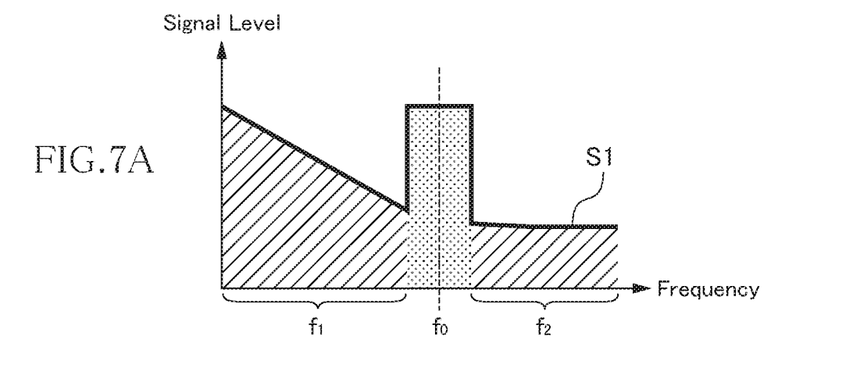
FIG. 7 is a diagram illustrating an operation in a case where the first signal generation unit 20 is a band elimination filter.
Figure 7B:
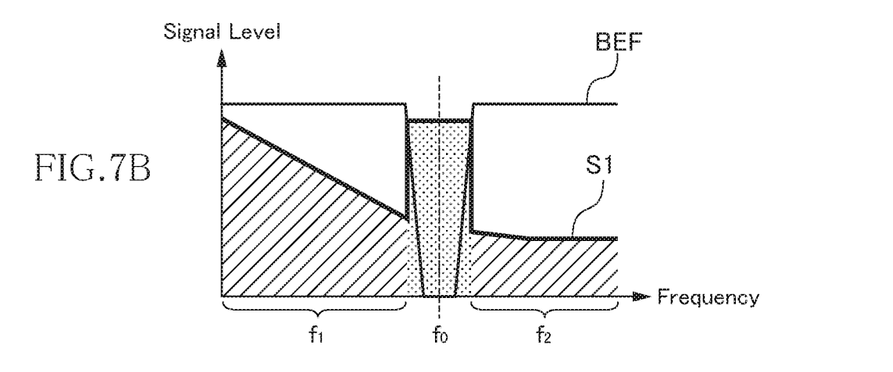
Figure 7C:
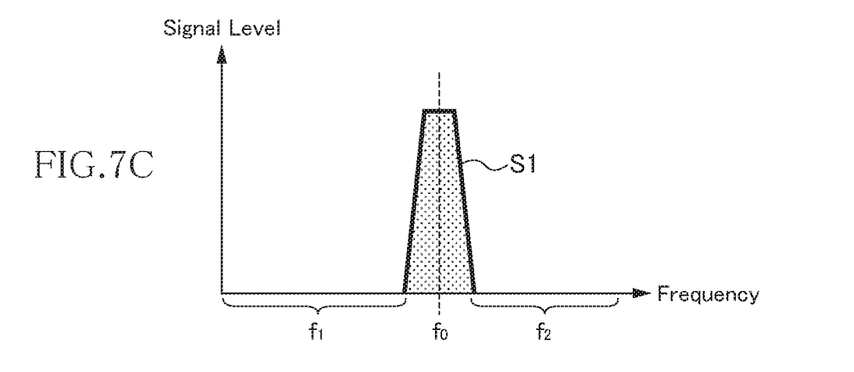

Also in the example illustrated in FIG. 7A, the frequency bands f1 and f2 away from the frequency f0 of the detection magnetic field are noise components. When a band elimination filter having characteristics BEF that allow the frequency bands f1 and f2 to pass is used as illustrated in FIG. 7B, the magnetic fields of the frequency bands f1 and f2 are canceled by the first magnetic field generation unit 40. As a result, the frequency components f1 and f2 are eliminated from the output signal S1 as illustrated in FIG. 7C, so that the S/N ratio becomes much higher than that of the original output signal S1.

FIG. 8 is a diagram illustrating an operation in a case where the first signal generation unit 20 is a high-pass filter.

Figure 8A:
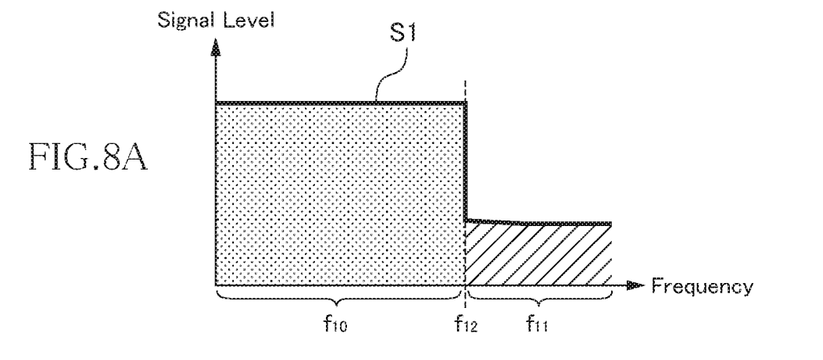
FIG. 8 is a diagram illustrating an operation in a case where the first signal generation unit 20 is a high-pass filter.

In this example, the output signal S1 has frequency components illustrated in FIG. 8A and the frequency band of the detection magnetic field is f10. The frequency band f10 of the detection magnetic field is a band equal to or lower than a frequency f12 and includes DC components. In this case, a frequency band f11 higher than the frequency f12 are noise components.

Figure 8B:
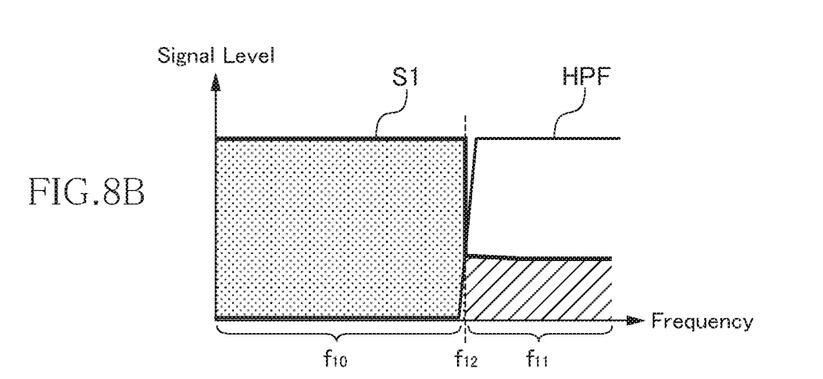
Figure 8C:
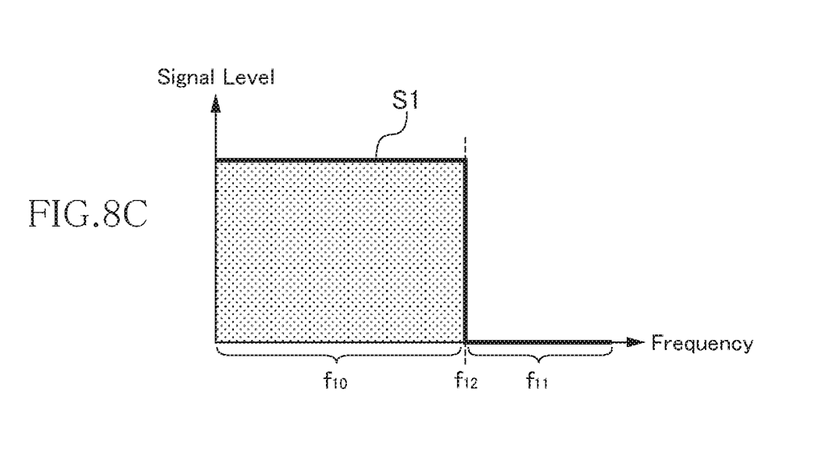

When a high-pass filter having characteristics HPF that allow the frequency band f11 to pass is used as illustrated in FIG. 8B, the magnetic field of the frequency band f11 is canceled by the first magnetic field generation unit 40. As a result, the frequency component f11 is eliminated from the output signal S1 as illustrated in FIG. 8C, and therefore the S/N ratio becomes higher than that of the original output signal S1. This example is effective when the frequency band f10 of the detection magnetic field is DC components or a low frequency, or when the frequency of the environmental magnetic field is higher than the frequency of the detection magnetic field.

FIG. 9 is a diagram illustrating an operation in a case where the first signal generation unit 20 is a band-pass filter.

Figure 9A:
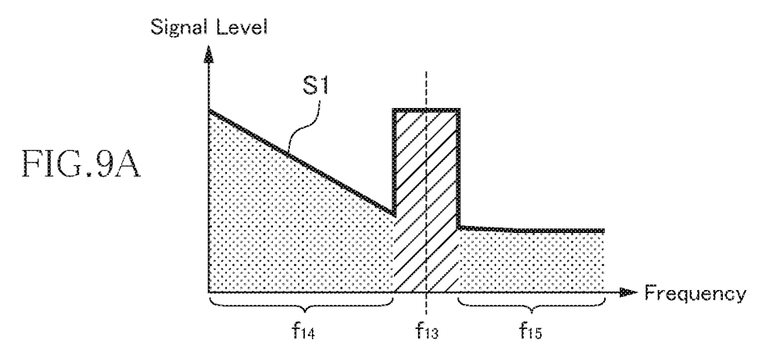
FIG. 9 is a diagram illustrating an operation in a case where the first signal generation unit 20 is a band-pass filter.

In this example, the output signal S1 has frequency components illustrated in FIG. 9A and the frequency band of noise components is f13. Frequency bands f14 and f15 other than the frequency band f13 are frequency bands of the detection magnetic field. The frequency band f13 can include a part of the detection magnetic field.

Figure 9B:
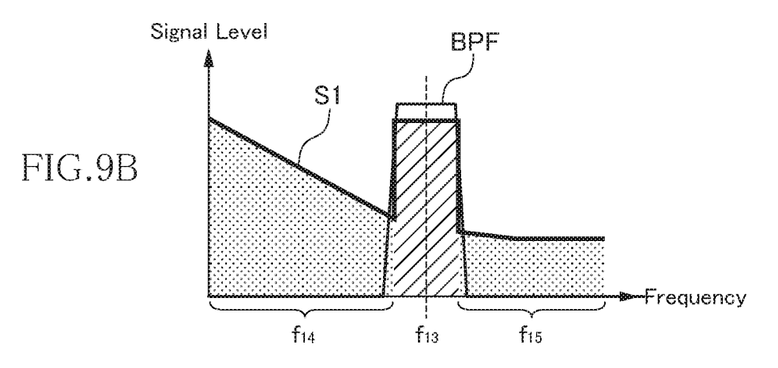
Figure 9C:
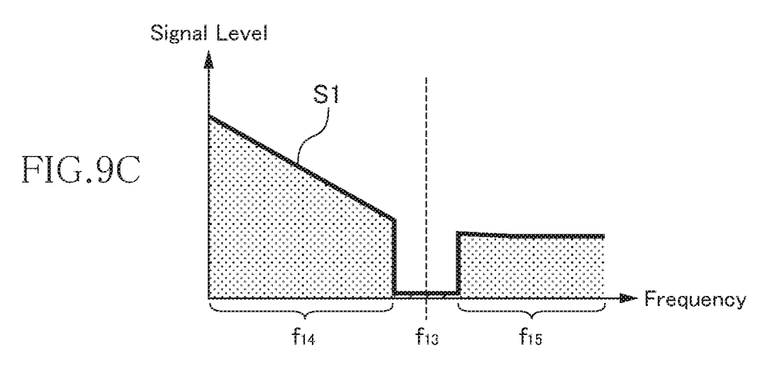

When a band-pass filter having characteristics BPF that allow the frequency band f13 to pass is used as illustrated in FIG. 9B, the magnetic field of the frequency band f13 is canceled by the first magnetic field generation unit 40. As a result, the frequency component f13 is eliminated from the output signal S1 as illustrated in FIG. 9C. When the frequency band f13 includes a part of the detection magnetic field, the part of the detection magnetic field is also eliminated by the first magnetic field generation unit 40. However, this results in increase of the S/N ratio when the noise components included in the frequency band f13 are intense. This example is effective when the frequency band of noise components is known in advance, as in the case of hum noise.

When the magnetic field detection device 100 according to the present embodiment is used in this way, the environmental magnetic field such as terrestrial magnetism is canceled by the first magnetic field generation unit 40. Therefore, only the detection magnetic field can be detected accurately. Further, because cancellation of the environmental magnetic field significantly reduces the absolute value of the magnetic field intensity applied to the magnetic field detection unit 10, saturation of the magnetic field detection unit 10 is prevented and highly sensitive detection can be performed.

Besides, because the canceling operation is realized by extracting frequency components corresponding to the environmental magnetic field, it is not necessary to use a plurality of the magnetic field detection units 10 and the number of parts can be reduced. Further, in the present embodiment, because the closed loop control using the second magnetic field generation unit 50 is executed, the detection magnetic field can be detected more accurately.

Figure 10:
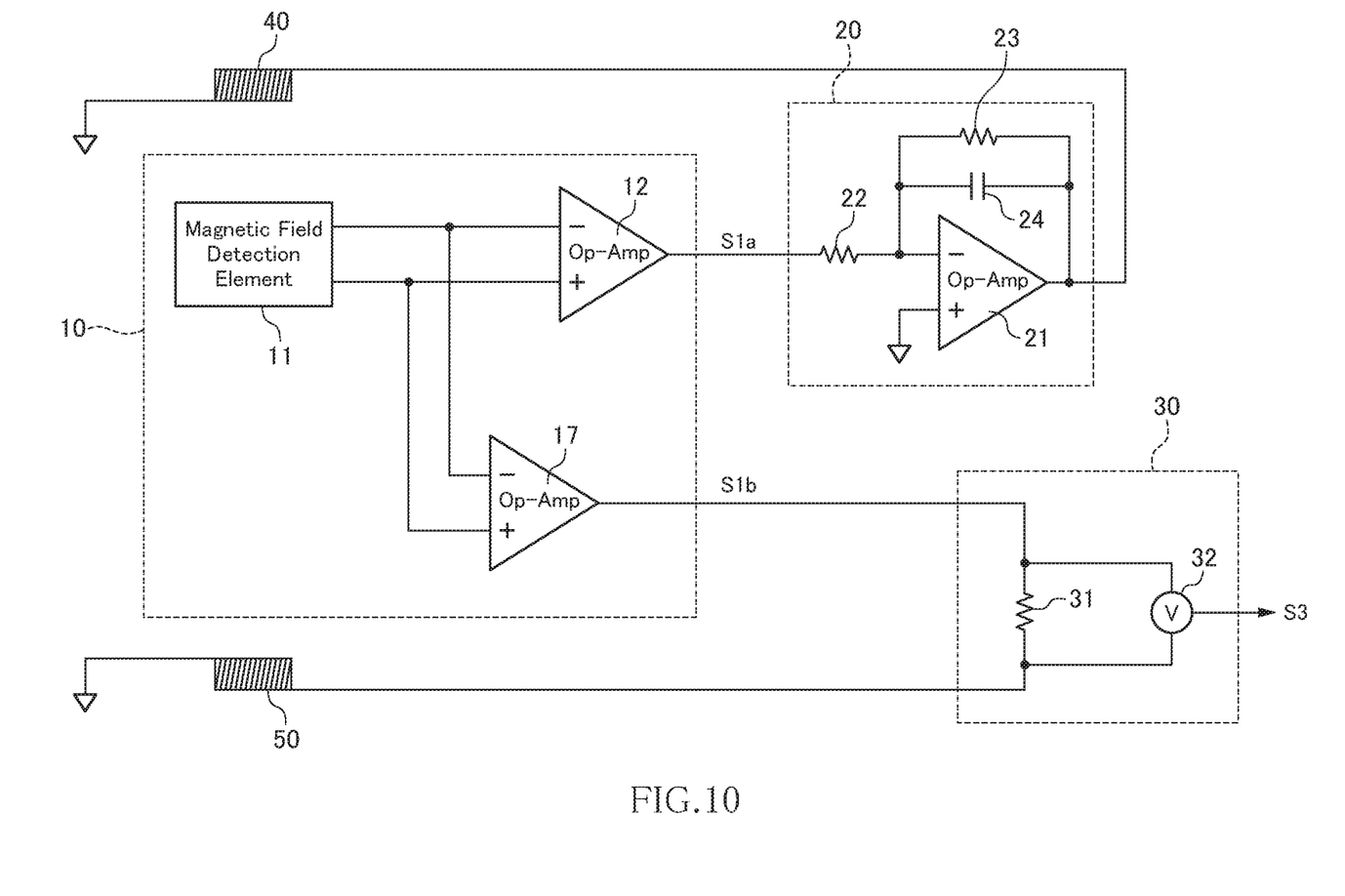
FIG. 10 is a circuit diagram illustrating another example of the specific configuration of the magnetic field detection device 100.

FIG. 10 is a circuit diagram illustrating another example of the specific configuration of the magnetic field detection device 100.

In the example illustrated in FIG. 10, another operational amplifier (an amplification circuit) 17 is added to the magnetic field detection unit 10. The operational amplifier 12 and the operational amplifier 17 are provided in parallel. An output signal S1a generated by the operational amplifier 12 is input to the first signal generation unit 20 and an output signal S1b generated by the operational amplifier 17 is input to the second signal generation unit 30. Other features of the example illustrated in FIG. 10 are identical to those in the circuit example illustrated in FIG. 2.

As the circuit illustrated in FIG. 10 is used, not only the load per operational amplifier is reduced but also elements included in the first signal generation unit 20 and elements included in the second signal generation unit 30 are prevented from being directly connected to each other. Therefore, a circuit constant of the first signal generation unit 20 and a circuit constant of the second signal generation unit 30 can be set independently from each other, and this setting facilitates circuit design.

A configuration of the magnetic field detection device 100 according to the present embodiment is explained next.

Figure 11:
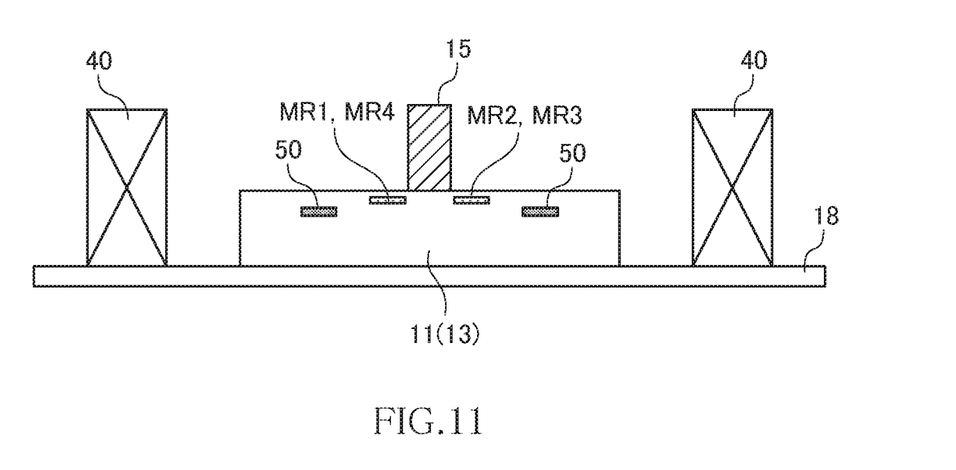
FIG. 11 is a schematic sectional view for explaining a configuration of the magnetic field detection device 100 according to a first example.
Figure 12:
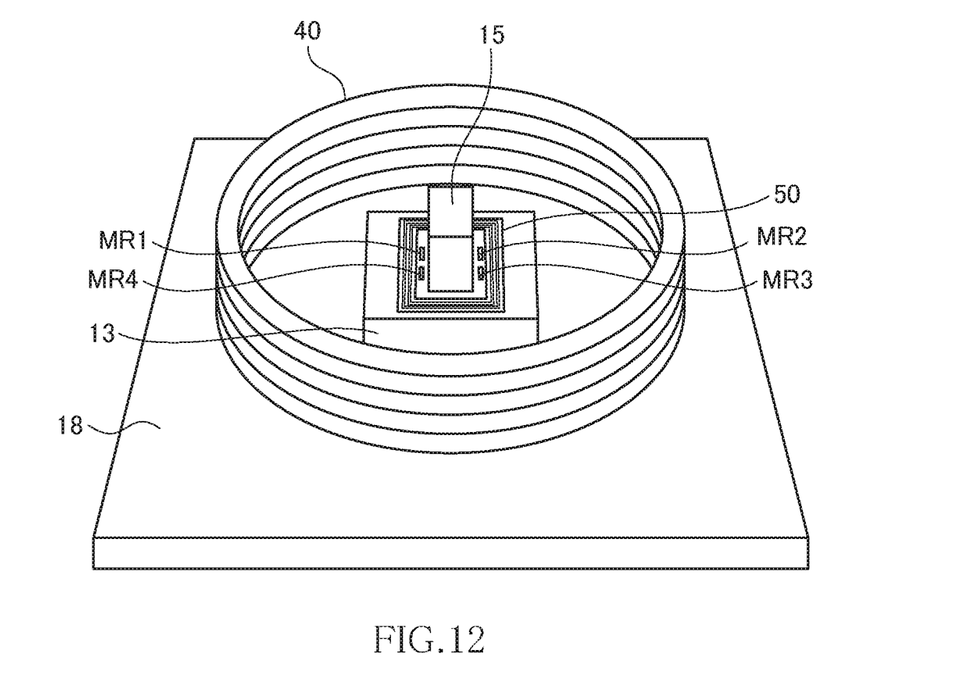
FIG. 12 is a schematic perspective view illustrating an external appearance of the magnetic field detection device 100 according to the first example.

FIG. 11 is a schematic sectional view for explaining a configuration of the magnetic field detection device 100 according to the first example, and FIG. 12 is a schematic perspective view illustrating an external appearance thereof.

In the examples illustrated in FIGS. 11 and 12, a sensor chip constituting the magnetic field detection element 11 and a coil constituting the first magnetic field generation unit 40 are mounted on a surface of a circuit substrate 18. The sensor chip is placed in an inner diameter portion of the coil constituting the first magnetic field generation unit 40 and a cancel magnetic field generated by the first magnetic field generation unit 40 is therefore applied to the sensor chip accurately and efficiently.

A coil constituting the second magnetic field generation unit 50 is embedded in the substrate 13 of the sensor chip. The coil constituting the second magnetic field generation unit 50 is placed to surround the magnetoresistive sensors MR1 to MR4 in planar view and a cancel magnetic field generated by the second magnetic field generation unit 50 is therefore applied to the sensor chip accurately and efficiently.

When the magnetoresistive sensors MR1 to MR4 constituting the magnetic field detection element 11 and the coil constituting the second magnetic field generation unit 50 are integrated on the same substrate 13 in this way, the number of parts can be further reduced. Further, because a large coil surrounding the sensor chip is used for the coil constituting the first magnetic field generation unit 40, the environmental magnetic field can be canceled sufficiently even if the environmental magnetic field is intense.

Figure 13:
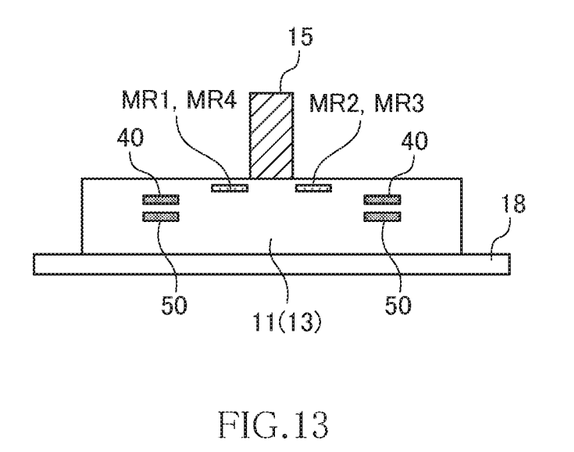
FIG. 13 is a schematic sectional view for explaining a configuration of the magnetic field detection device 100 according to a second example.

FIG. 13 is a schematic sectional view for explaining a configuration of the magnetic field detection device 100 according to the second example.

In the example illustrated in FIG. 13, not only the coil constituting the second magnetic field generation unit 50 but also the coil constituting the first magnetic field generation unit 40 is integrated on the sensor chip. This can further reduce the number of parts and a coil using a wire or the like is not required, so that the entire size of the device can be reduced.

Figure 14:
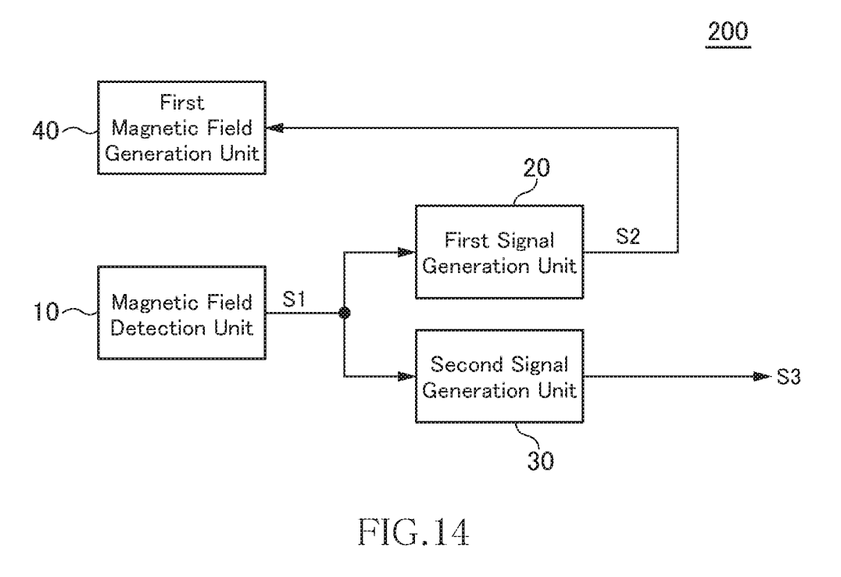
FIG. 14 is a block diagram illustrating a configuration of a magnetic field detection device 200 according to a second embodiment of the present invention.
Figure 15:
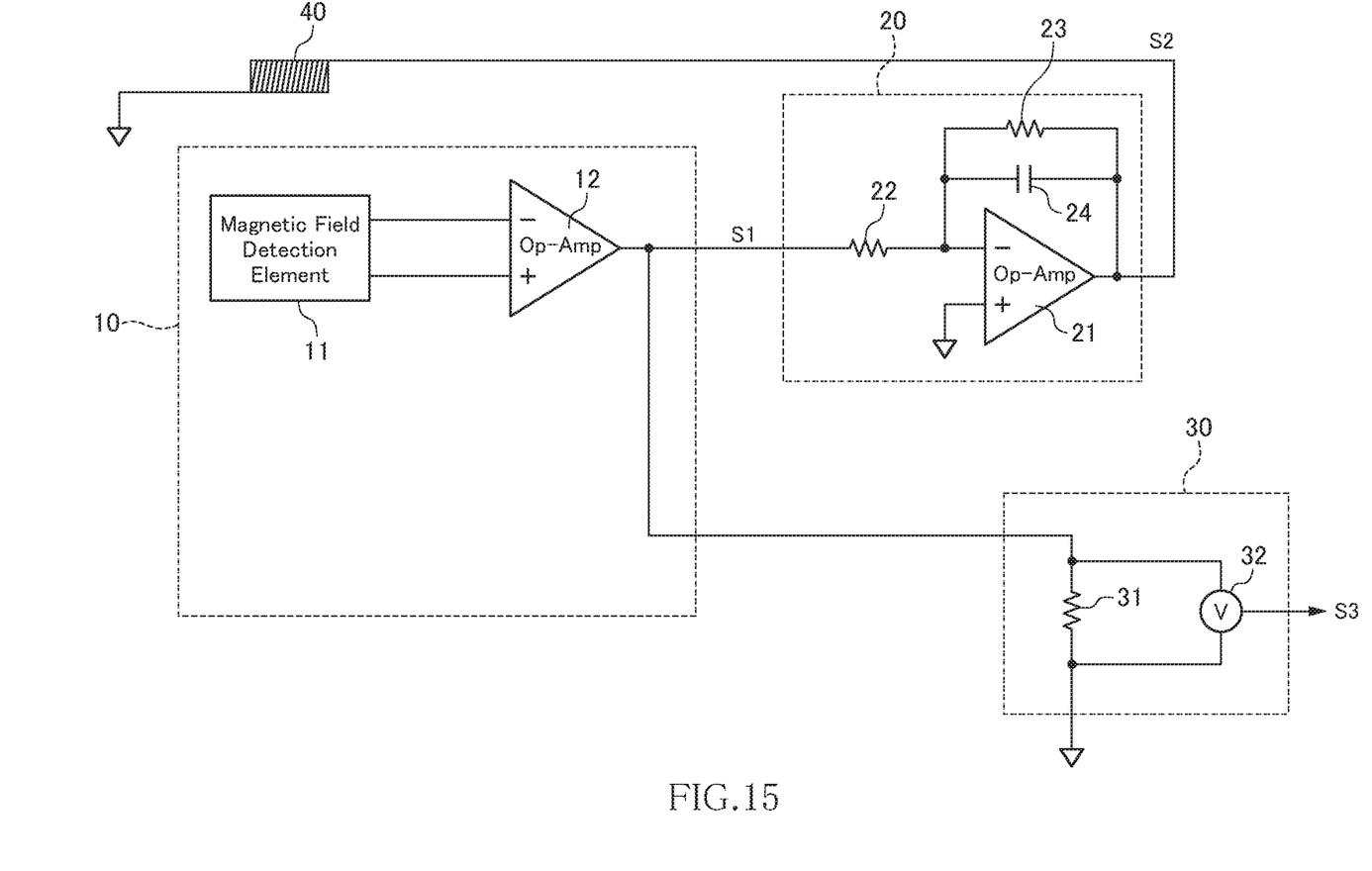
FIG. 15 is a circuit diagram illustrating an example of a specific configuration of the magnetic field detection device 200.

FIG. 14 is a block diagram illustrating a configuration of a magnetic field detection device 200 according to the second embodiment of the present invention. FIG. 15 is a circuit diagram illustrating an example of a specific configuration of the magnetic field detection device 200.

As illustrated in FIGS. 14 and 15, the magnetic field detection device 200 according to the present embodiment is different from the magnetic field detection device 100 according to the first embodiment illustrated in FIGS. 1 and 2 in that the second magnetic field generation unit 50 is omitted. Other features of the magnetic field detection device 200 according to the second embodiment are identical to those of the magnetic field detection device 100 according to the first embodiment, and thus like elements are denoted by like reference characters and redundant explanations thereof will be omitted.

Because the second magnetic field generation unit 50 is omitted from the magnetic field detection device 200 according to the present embodiment, the detection magnetic field is not canceled. However, the detection signal S3 can be generated by so-called open loop control. In addition, according to the present embodiment, the number of parts can be further reduced as compared to the magnetic field detection device 100 according to the first embodiment.

It is apparent that the present invention is not limited to the above embodiments, but may be modified and changed without departing from the scope and spirit of the invention.

For example, in the embodiments described above, the first signal generation unit 20 is constituted by a low-pass filter using an operational amplifier. However, the configuration of the low-pass filter is not limited thereto, and a low-pass filter using an integrator can be used, or a low-pass filter using an A/D converter that converts the output signal S1 into a digital signal and a digital filter that processes digital signal can be used.

Further, the first signal generation unit 20 does not need to be a low-pass filter, and it can be a band elimination filter as explained with reference to FIG. 7, a high-pass filter as explained with reference to FIG. 8, and a band-pass filter as explained with reference to FIG. 9.

REFERENCE SIGNS LIST 10 magnetic field detection unit
11 magnetic field detection element
12 operational amplifier (first amplification circuit)
13 substrate
14 insulating layer
15 magnetic member
16 constant voltage source
17 operational amplifier (second amplification circuit)
18 circuit substrate
20 first signal generation unit
21 operational amplifier
22, 23 resistor
24 capacitor
30 second signal generation unit
31 resistor
32 voltage detection circuit
40 first magnetic field generation unit
50 second magnetic field generation unit
100, 200 magnetic field detection device
E1-E4 terminal electrode
MR1-MR4 magnetoresistive sensor
S1 output signal
S2 cancel signal
S3 detection signal
Ø magnetic flux

What is claimed is:

1. A magnetic field detection device comprising:
    a magnetic field detection unit that generates an output signal according to a magnetic field;
    a first signal generation unit that extracts a predetermined frequency component from the output signal and generates a cancel signal based on the predetermined frequency component;
    a first magnetic field generation unit that applies a first cancel magnetic field to the magnetic field detection unit based on the cancel signal; and
    a second signal generation unit that generates a detection signal based on the output signal of the magnetic field detection unit to which the first cancel magnetic field is applied, and
    a second magnetic field generation unit that applies a second cancel magnetic field to the magnetic field detection unit based on the output signal of the magnetic field detection unit to which the first cancel magnetic field is applied,
    wherein the output signal of the magnetic field detection unit supplied to the second magnetic field generation unit is an input signal of the first signal generation unit, thereby the first and second magnetic field generation units are supplied with different signals, respectively.

2. The magnetic field detection device as claimed in claim 1, wherein the predetermined frequency component includes a DC component.

3. The magnetic field detection device as claimed in claim 1, wherein the first signal generation unit includes a low-pass filter, a band elimination filter, a high-pass filter, or a band-pass filter.

4. The magnetic field detection device as claimed in claim 1, wherein the first signal generation unit includes an A/D converter that converts the output signal into a digital signal, and a digital filter that processes the digital signal.

5. The magnetic field detection device as claimed in claim 1, wherein the first magnetic field generation unit includes a first coil, and wherein the magnetic field detection unit is placed in an inner diameter portion of the first coil.

6. The magnetic field detection device as claimed in claim 1, wherein the magnetic field detection unit includes a magnetic field detection element that converts the magnetic field into a potential difference, and a first amplification circuit that amplifies the potential difference to generate the output signal.

7. The magnetic field detection device as claimed in claim 6, wherein the magnetic field detection element and the second magnetic field generation unit are integrated on a same sensor chip.

8. The magnetic field detection device as claimed in claim 7, wherein the first magnetic field generation unit is further integrated on the sensor chip.

9. The magnetic field detection device as claimed in claim 6, wherein the magnetic field detection unit further includes a second amplification circuit that is provided separately from the first amplification circuit and that amplifies the potential difference to generate the detection signal.

10. The magnetic field detection device as claimed in claim 1,
    wherein the first magnetic field generation unit includes a first coil, and
    wherein the magnetic field detection unit is surrounded by the first coil.

11. The magnetic field detection device as claimed in claim 10, further comprising a sensor chip that integrates the magnetic field detection unit and the second magnetic field generation unit, wherein the sensor chip is surrounded by the first coil.

12. The magnetic field detection device as claimed in claim 11, further comprising a circuit substrate on which the sensor chip and the first coil are mounted.

* * * * *